(12) United States Patent
Astwood et al.

(10) Patent No.: US 9,445,619 B2
(45) Date of Patent: *Sep. 20, 2016

(54) COMPOSITIONS AND METHODS FOR UTILIZATION OF ALGAL COMPOUNDS

(71) Applicants: James Astwood, Alameda, CA (US); Michelle L. Collins, Oakland, CA (US); Brian Connolly, Hayward, CA (US)

(72) Inventors: James Astwood, Alameda, CA (US); Michelle L. Collins, Oakland, CA (US); Brian Connolly, Hayward, CA (US)

(73) Assignee: AURORA ALGAE, INC., Hayward, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/025,772

(22) Filed: Sep. 12, 2013

(65) Prior Publication Data

US 2014/0271706 A1 Sep. 18, 2014

Related U.S. Application Data

(60) Provisional application No. 61/800,114, filed on Mar. 15, 2013, provisional application No. 61/800,029, filed on Mar. 15, 2013.

(51) Int. Cl.

| | |
|---|---|
| A23L 1/30 | (2006.01) |
| A61K 31/201 | (2006.01) |
| A61K 31/202 | (2006.01) |
| A61K 31/661 | (2006.01) |
| A61K 31/7028 | (2006.01) |
| A61K 36/02 | (2006.01) |
| C12N 15/82 | (2006.01) |
| C12P 7/64 | (2006.01) |
| A61K 31/231 | (2006.01) |
| A61K 31/683 | (2006.01) |
| A61K 31/7012 | (2006.01) |
| C11C 1/02 | (2006.01) |
| C11B 3/00 | (2006.01) |
| C11C 3/08 | (2006.01) |
| A23D 9/00 | (2006.01) |
| A21D 2/16 | (2006.01) |
| A61K 31/20 | (2006.01) |
| A23L 1/337 | (2006.01) |
| A23L 2/04 | (2006.01) |

(52) U.S. Cl.
CPC .......... *A23L 1/3008* (2013.01); *A21D 2/165* (2013.01); *A23D 9/00* (2013.01); *A23L 1/3006* (2013.01); *A23L 1/337* (2013.01); *A23L 2/04* (2013.01); *A61K 31/20* (2013.01); *A61K 31/201* (2013.01); *A61K 31/202* (2013.01); *A61K 31/231* (2013.01); *A61K 31/661* (2013.01); *A61K 31/683* (2013.01); *A61K 31/7012* (2013.01); *A61K 31/7028* (2013.01); *A61K 36/02* (2013.01); *C11B 3/001* (2013.01); *C11C 1/02* (2013.01); *C11C 3/08* (2013.01); *C12N 15/8247* (2013.01); *C12P 7/6427* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 3,642,844 A | 2/1972 | Forbes | |
| 5,656,667 A | 8/1997 | Breivik et al. | |
| 6,541,519 B2 * | 4/2003 | Collin et al. | 514/558 |
| 2003/0100603 A1 * | 5/2003 | Beinlich et al. | 514/458 |
| 2004/0091524 A1 | 5/2004 | Tanaka et al. | |
| 2009/0181438 A1 | 7/2009 | Sayre | |
| 2009/0311367 A1 | 12/2009 | Perry | |
| 2010/0069492 A1 * | 3/2010 | Geiringen et al. | 514/560 |
| 2011/0197306 A1 | 8/2011 | Bailey et al. | |
| 2012/0225941 A1 | 9/2012 | Green | |
| 2013/0046020 A1 | 2/2013 | Liang et al. | |
| 2013/0129775 A1 | 5/2013 | Shinde et al. | |
| 2014/0273113 A1 | 9/2014 | Vick et al. | |
| 2014/0274922 A1 | 9/2014 | van der Meulen et al. | |
| 2014/0275483 A1 | 9/2014 | Hippler et al. | |
| 2014/0275596 A1 | 9/2014 | Astwood et al. | |
| 2014/0275613 A1 | 9/2014 | Hippler et al. | |

FOREIGN PATENT DOCUMENTS

| | | |
|---|---|---|
| CN | 105209034 | 12/2015 |
| CN | 105263896 A | 1/2016 |
| EP | 2968244 | 1/2016 |
| IN | 9376/DELNP/2015 | 2/2016 |
| IN | 9377/DELNP/2015 | 2/2016 |
| WO | WO2014151110 | 9/2014 |

(Continued)

OTHER PUBLICATIONS 2010 http://www.niams.nih.gov/health_info/autoinflammatory/.*

(Continued)

*Primary Examiner* — Catheryne Chen
(74) *Attorney, Agent, or Firm* — Carr & Ferrell LLP

(57) ABSTRACT

Provided herein are exemplary compositions, products, and capsules utilizing POA, EPA, blends of POA and EPA, total algal oil compositions, and/or whole biomass compositions in methods of inhibiting inflammation including in cardiovascular disease, diabetes, obesity, stroke, metabolic syndromes, dementia, Alzheimer's disease, and/or cancer. The exemplary compositions, products, and capsules may be orally, topically, intravenously, and/or subcutaneously administered. The exemplary compositions herein may be used as feed, food, food supplements, beverages, beverage supplements, nutritional products, products for athletic performance, pharmaceutical products, and/or medical products for mammalian use, including humans.

14 Claims, 1 Drawing Sheet

(56) References Cited

FOREIGN PATENT DOCUMENTS

| WO | WO2014151113 | 9/2014 |
|---|---|---|
| WO | WO2014151116 | 9/2014 |

OTHER PUBLICATIONS

Metin, S., & Hartel, R. (2005). Fat crystallization technology. Healthful Lipids. AOCS Press, Champaign, 145-170.

El-Shoubaky, G. A., Moustafa, A. M. Y., & Salem, E. A. E. (2008). Comparative Phytochemical Investigation of Beneficial Essential Fatty Acids on a Variety of Marine Seaweeds Algae. Research Journal of Phytochemistry, 2(1), 18-26.

Jacobson, T. A., Glickstein, S. B., Rowe, J. D., & Soni, P. N. (2012). Effects of eicosapentaenoic acid and docosahexaenoic acid on low-density lipoprotein cholesterol and other lipids: a review. Journal of Clinical Lipidology, 6 (1), 5-18.

Chisholm, M.J., & Hopkins, C.Y. (1965). Fatty acids of Doxantha seed oil. Journal of the American Oil Chemists' Society, 42(1), 49-50.

Kitano, M., Matsukawa, R., & Karube, I. (1998). Enhanced eicosapentaenoic acid production by Navicula saprophila. Journal of applied phycology, 10(1), 101-105.

International Search Report and Written Opinion of the International Searching Authority mailed Jul. 1, 2014 for Application No. PCT/US2014/025012, filed Mar. 12, 2014.

International Search Report and Written Opinion of the International Searching Authority mailed Jul. 7, 2014 for Application No. PCT/US2014/025019, filed Mar. 12, 2014.

International Search Report and Written Opinion of the International Searching Authority mailed Aug. 5, 2014 for Application No. PCT/US2014/025007, filed Mar. 12, 2014.

Krienitz et al. "The high content of polyunsaturated fatty acids in Nannochloropsis limnetica (Eustigmatophyceae) and its implication for food web interactions, freshwater aquaculture and biotechnology." Limnologica. vol. 36. Sep. 29, 2006. pp. 204-210.

Hu et al. "Optimization of Growth and Fatty Acid Composition of a Unicellular Marine Picoplankton, Nannochloropsis sp., with Enriched Carbon Sources", Biotechnology Letters, 25(5): 421-425 (2003).

Pal et al. "The Effect of Light, Salinity, and Nitrogen Availability on Lipid Production by Nannochloropsis sp.", Appl Microbiol Biotechnol, 90:1429-1441 (2011).

Patil et al., "Fatty Acid Composition of 12 Microalgae for Possible use in Aquaculture Feed." Aquae Int, vol. 15, No. 1, pp. 1-9 (2007).

Wagenen et aL, "Effects of Light and Temperature on Fatty Acid Production in Nannochloropsis Salina", Energies, vol. 5, No. 3 pp. 731-740 2012.

Frankel, Arthur E., "Immunotoxins" "Springer Science & Business Media, Dec. 6, 2012 at p. 418 on the web atbooks.goog le.com/books ?id=zbfdBgAAQBAJ&dq= IC R-1 91 +and+phenotype&sou rce=gbs navlinks s".

Krientiz et al. Limnologica—Ecology and Management of Inland Waters vol. 36, Issue 3, Sep. 29, 2006, pp. 204-210.

Office Action mailed Jul. 19, 2016 in Chinese Application No. 201480024225.9 filed Mar. 12, 2014.

* cited by examiner

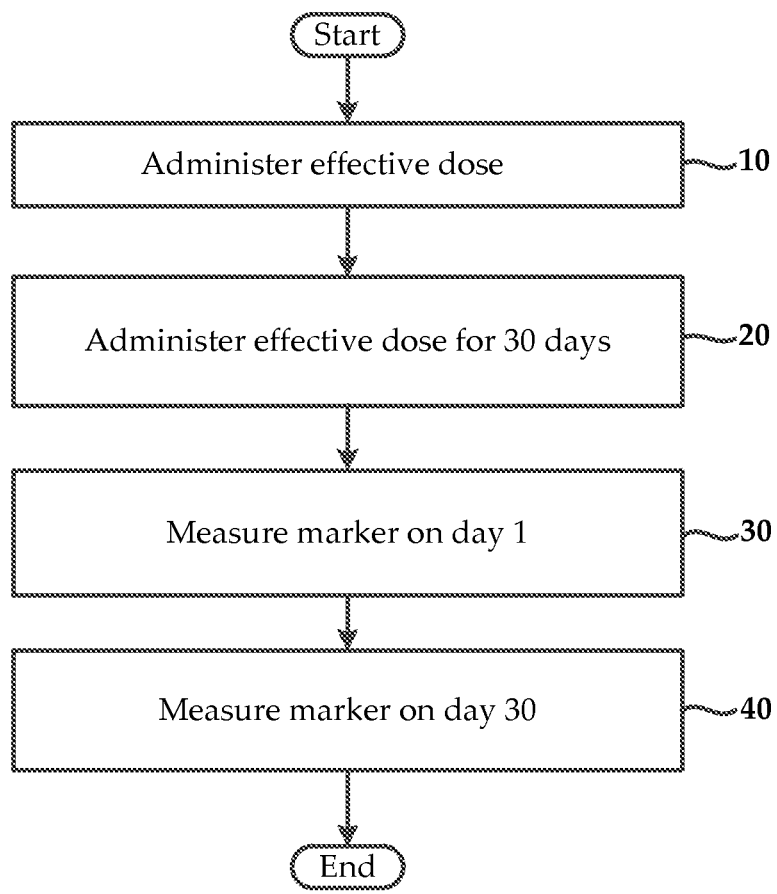

COMPOSITIONS AND METHODS FOR UTILIZATION OF ALGAL COMPOUNDS

CROSS-REFERENCE TO RELATED APPLICATIONS

The present application claims the benefit and priority of U.S. Provisional Patent Application Ser. No. 61/800,114 filed on Mar. 15, 2013 and titled "(EPA) Algal Biomass and Oil Compositions and Impact on Health," which is hereby incorporated by reference.

The present application claims the benefit and priority of U.S. Provisional Patent Application Ser. No. 61/800,029 filed on Mar. 15, 2013 and titled "Microalga Species and Industrial Applications," which is hereby incorporated by reference.

The present application is related to U.S. Non-Provisional patent application Ser. No. 14/025,766 filed on Sep. 12, 2013 concurrently with the present application and titled "Algal Omega 7 Compositions," which is hereby incorporated by reference.

The present application is related to U.S. Non-Provisional patent application Ser. No. 14/025,762 filed on Sep. 12, 2013 concurrently with the present application and titled "Algal Oil Compositions," which is hereby incorporated by reference.

The present application is related to U.S. Non-Provisional patent application Ser. No. 14/025,740 filed on Sep. 12, 2013 concurrently with the present application and titled "Conversion of Free Fatty Acids to Ethyl Esters," which is hereby incorporated by reference.

The present application is related to U.S. Non-Provisional patent application Ser. No. 14/025,756 filed on Sep. 12, 2013 concurrently with the present application and titled "Algal Omega 7 and Algal Omega 3 Blend Compositions," which is hereby incorporated by reference.

BACKGROUND OF THE INVENTION

Field of the Invention

This invention relates to algal biochemistry, and more specifically, to algal compositions and methods of utilization.

SUMMARY OF THE INVENTION

Provided herein are exemplary products for mammalian consumption selected from any of a composition comprising by dry weight approximately 20% to approximately 97% algal C20:5 n3 Eicosapentaenoic acid (EPA), a composition comprising by dry weight approximately 17% to approximately 90% algal C16:1 n7 palmitoleic acid (POA) and less than approximately 10% algal saturated fatty acids, a composition comprising by dry weight approximately 17% to approximately 90% algal C16:1 n7 palmitoleic acid (POA) and substantially no algal saturated fatty acids, a composition comprising a blend by dry weight of approximately 20% to approximately 97% algal C20:5 n3 Eicosapentaenoic acid (EPA) and approximately 17% to approximately 90% algal C16:1 n7 palmitoleic acid (POA), a total algal oil composition comprising by total weight at least 20% algal EPA, at least 17% algal POA, approximately 0% to 20% algal saturated fats, less than approximately 10% algal ARA, and substantially no algal DHA, a total algal oil composition comprising by total weight at least 20% algal EPA, at least 17% algal POA, less than approximately 10% ARA, and substantially no algal DHA and substantially no algal saturated fatty acids, or an algal biomass composition comprising at least approximately 10% algal lipids, at least approximately 15% algal carbohydrates, at least approximately 25% algal protein, at least approximately 3% moisture and at least approximately 5% ash. The exemplary products may further comprise feed products, food products, food supplements, dietary products, compositions and/or products for athletic performance, pharmaceutical products, nutritional products, beverage products, or beverage supplement products. The exemplary products may be in a form of an ethyl ester (EE), a mono, di, or triacylglycerol (MAG, DAG, TAG), a phospholipid (PL), a galactolipid (GL), free fatty acid (FFA), or a sulfoquinovosyl diacylglycerol (SQDG).

Also provided herein are exemplary methods for inhibiting inflammation of tissue of a mammalian subject, the method comprising administering at an effective dose a selected composition from any of a composition comprising by dry weight approximately 20% to approximately 97% algal C20:5 n3 Eicosapentaenoic acid (EPA), a composition comprising by dry weight approximately 17% to approximately 90% algal C16:1 n7 palmitoleic acid (POA) and less than approximately 10% algal saturated fatty acids, a composition comprising by dry weight approximately 17% to approximately 90% algal C16:1 n7 palmitoleic acid (POA) and substantially no algal saturated fatty acids, a composition comprising a blend by dry weight of approximately 20% to approximately 97% algal C20:5 n3 Eicosapentaenoic acid (EPA) and approximately 17% to approximately 90% algal C16:1 n7 palmitoleic acid (POA), a total algal oil composition comprising by total weight at least 20% algal EPA, at least 17% algal POA, approximately 0% to 20% algal saturated fats, less than approximately 10% ARA, and substantially no algal DHA, or a total algal oil composition comprising by total weight at least 20% algal EPA, at least 17% algal POA, less than approximately 10% ARA, and substantially no algal DHA and substantially no algal saturated fatty acids. According to some exemplary methods, the effective dose is approximately between 20 milligrams per day and 5 grams per day, and/or may include administering the selected composition for a treatment period of at least 30 days and/or measuring a clinical marker of inflammation on a first day of administration. According to some exemplary methods, the clinical markers may include any of weight, triglyceride level, total cholesterol, low-density lipoprotein, high-density lipoprotein, C-reactive protein, adiponectin, fatty acids, tumor necrosis factor alpha, C-peptide, monocyte chemoattractant protein-1, insulin level, ghrelin, leptin or glucagon. The exemplary methods may further comprise measuring a clinical marker of inflammation on day 30, with the clinical marker measurement indicating an improvement relative to a clinical marker measurement made before day 30. According to some exemplary methods, inflammatory diseases may include cardiovascular diseases, diabetes, obesity, stroke, a metabolic syndrome, dementia, Alzheimer's disease, and/or cancer.

Provided herein is a capsule comprising at least approximately 50 milligrams selected from any of a composition comprising by dry weight approximately 20% to approximately 97% algal C20:5 n3 Eicosapentaenoic acid (EPA), a composition comprising by dry weight approximately 17% to approximately 90% algal C16:1 n7 palmitoleic acid (POA) and less than approximately 10% algal saturated fatty acids, a composition comprising by dry weight approximately 17% to approximately 90% algal C16:1 n7 palmitoleic acid (POA) and substantially no algal saturated fatty acids, a composition comprising a blend by dry weight of approximately 20% to approximately 97% algal C20:5 n3 Eicosapentaenoic acid (EPA) and approximately 17% to approximately 90% algal C16:1 n7 palmitoleic acid (POA); and/or a total algal oil composition comprising by total weight at least 20% algal EPA, at least 17% algal POA, less than approximately 10% algal ARA, and substantially no algal DHA and substantially no algal saturated fatty acids. According to some exemplary capsules, the capsule may be a nutritional capsule, a medical capsule, or a pharmaceutical capsule. In yet further exemplary capsules, the capsule may comprise an antioxidant.

Provided herein are exemplary methods for reducing chronic inflammation and weight associated with obesity in a human, the method comprising orally administering on a daily basis for a treatment period of at least 30 days with at least one capsule having at least 25% of its capsule volume comprising a composition further comprising by dry weight approximately 90% palmitoleic acid, less than approximately 0.5% saturated fatty acids, less than approximately 2% arachidonic acid, substantially no docosahexaenoic acid, and less than approximately 10% eicosapentaenoic acid, wherein the composition is in a form of an ethyl ester (EE), a mono, di, or triacylglycerol (MAG, DAG, TAG), a phospholipid (PL), a galactolipid (GL), free fatty acid (FFA), or a sulfoquinovosyl diacylglycerol (SQDG).

BRIEF DESCRIPTION OF THE DRAWINGS

FIG. 1 is a flow chart of an exemplary method for inhibiting inflammation of tissue of a mammalian subject.

DETAILED DESCRIPTION OF THE INVENTION

A fatty acid is a carboxylic acid with a long aliphatic tail (chain), which is either saturated or unsaturated. Most naturally occurring fatty acids have a chain of an even number of carbon atoms, from 4 to 28. Saturated fatty acids have no double bonds between carbon atoms. Unsaturated fatty acids have one or more double bonds between carbon atoms. When counting from the terminal methyl carbon toward the carbonyl carbon on an unsaturated fatty acid, the first double bond signifies the omega double bond, such as observed in omega 3, omega 6, or omega 7 fatty acids.

Palmitoleic acid (POA) is an omega-7 monounsaturated fatty acid with a 16-carbon chain with one double bond, denoted as C16:1 n7. A beneficial fatty acid, it has been shown to suppress inflammation. Dietary sources of omega-7 are found in animal and plant sources, including sea buckthorn berries, macadamia nuts, cold water fish and dairy fat. These sources, however, are not concentrated and/or purified sources of POA and often contain a mixed fatty acid profile of saturated and polyunsaturated fats.

Palmitic acid (PA) is a saturated fatty acid with a 16-carbon chain and no double bonds, denoted as C16:0. Consumption of saturated fats such as palmitic acid is believed to increase the risk of developing inflammation and/or inflammatory-related health problems, including diabetes, obesity, stroke and cardiovascular diseases.

Alpha linolenic acid (ALA) is an omega-3 polyunsaturated fatty acid (PUFA) with an 18-carbon chain and three cis double bonds. The first double bond is located at the third carbon from the methyl end of the fatty acid chain, denoted as C18:3 n3.

Oleic acid (OA) is an omega-9 monounsaturated fatty acid with an 18-carbon chain with one double bond denoted as C18:1 n9. OA is a main component of olive oil, macadamia oil and other monounsaturated fats.

Arachidonic acid (ARA) is an omega-6 PUFA with a 20-carbon chain and four cis-double bonds; the first double bond is located at the sixth carbon from the omega end. ARA is also denoted as C20:4 n6. Examples of dietary sources of omega-6 PUFAs include refined vegetable oils, such as corn and soy oil, seeds and nuts and the oils extracted from them. Consumption is therefore sufficient in the average diet.

Eicosapentaenoic acid (EPA) is an omega-3 fatty acid PUFA with the following connotation C20:5 n3. It is a carboxylic acid with a 20-carbon chain and five cis double bonds; the first double bond is located at the third carbon from the omega end.

Docosahexaenoic acid (DHA) is an omega-3 fatty acid PUFA. It is a carboxylic acid with a 22-carbon chain and six cis double bonds; the first double bond is located at the third carbon from the omega end. DHA is also denoted as C22:6 n3

Additionally, the various algal compositions provided herein may further be in ethyl ester form. Such ethyl esters are derived by reacting free fatty acids with ethanol. Called esterification, the resulting ethyl ester allows for the fractional distillation (concentration) of the long chain fatty acids at lower temperatures. This step allows for the selective concentration of the fatty acids to levels greater than found in nature.

The ethyl ester forms of the various exemplary algal compositions provided herein may be converted to a triglyceride form by performing an enzymatic reaction with the ethyl ester form in the presence of glycerol, heating under a vacuum, and filtering out the enzymes. Per some exemplary methods, immobilized lipase enzymes such as those isolated from *Candida antarctica* are commercially available from companies such as Novozyme or Sigma Aldrich.

The exemplary compositions herein may include algal fatty acid compositions comprising by dry weight from about approximately 0.5% to about approximately 99% C16:1 n7 palmitoleic acid (POA). Such algal compositions may also include (either individually or any combination of) by dry weight: from about approximately 0% to about approximately 99% saturated fatty acids; from about approximately 0% to about approximately 99% arachidonic acid; from about approximately 0% to about 99% docosahexaenoic acid; and/or from about approximately 0% to about approximately 99% eicosapentaenoic acid.

The exemplary compositions herein may include algal fatty acid compositions comprising by dry weight from about approximately 0.5% to about approximately 99% C16:1 n7 palmitoleic acid (POA). Such algal compositions may also include (either individually or any combination of) by dry weight: from about approximately 0% to about approximately 10% saturated fatty acids; from about approximately 0% to about approximately 2% arachidonic acid; substantially no (i.e. less than approximately 0.5%) docosahexaenoic acid; and/or from about approximately 0% to about approximately 10% eicosapentaenoic acid.

The exemplary compositions herein may include algal fatty acid compositions having by dry weight about approximately 90% palmitoleic acid, less than about approximately 10% saturated fatty acids, less than about approximately 2% arachidonic acid, substantially no docosahexaenoic acid, and less than about approximately 10% eicosapentaenoic acid.

The exemplary compositions herein may comprise an algal composition comprising by dry weight at least approximately 50% C16:1 n7 palmitoleic acid and less than approximately 10% saturated fatty acids.

The exemplary compositions herein may include total algal oil compositions comprising by total weight between approximately 0% and 99% EPA, and one or more of the following: between approximately 0% and 99% POA, less than approximately 20% saturated fats (including 0% saturated fats or substantially saturated fat free), between approximately 0% and 99% ARA, and/or between approximately 0% and 99% DHA. According to further exemplary total algal oil compositions, the saturated fats may comprise PA.

The exemplary compositions herein may include total algal oil compositions comprising by total weight between approximately 0% and 99% OA and none, or one or more of the following: between approximately 0% and 99% EPA, between approximately 0% and 99% POA, less than approximately 20% saturated fats (including 0% saturated fats or substantially saturated fat free), between approximately 0% and 99% ARA, and/or between approximately 0% and 99% DHA. According to further exemplary total algal oil compositions, the saturated fats may comprise PA.

The exemplary compositions herein may include total algal oil compositions comprising by total weight at least 20% EPA and one or more of the following: at least 17% POA, at least 13% PA, less than approximately 10% ARA, and/or substantially no DHA.

The exemplary compositions herein may include total algal oil compositions comprising by total weight at least approximately 30% EPA and one or more of the following: at least approximately 27% POA, at least approximately 23% PA, less than approximately 10% ARA, and/or substantially no DHA.

The exemplary compositions herein may include algal fatty acid compositions comprising by dry weight approximately 0.5% to approximately 99% C20:5 n3 Eicosapentaenoic acid (EPA) and approximately 0.5% to approximately 99% C16:1 n7 palmitoleic acid (POA). Further exemplary algal fatty acid compositions may comprise (in addition to the above) one or more of the following by dry weight: between approximately 0% and 99% arachidonic acid; between approximately 0% and 99% docosahexaenoic acid; and/or less than approximately 20% saturated fatty acids (including 0% saturated fatty acids or substantially saturated fatty acid free). According to further exemplary total algal oil compositions, the saturated fats may comprise PA. Further exemplary saturated fatty acyl moiety-rich algal compositions may be in a form of an ethyl ester (EE), a mono, di- or triacylglycerol (MAG, DAG, TAG), a phospholipid (PL), a galactolipid (GL), free fatty Acid (FFA), or a sulfoquinovosyl diacylglycerol (SQDG).

The exemplary compositions herein may include algal fatty acid compositions comprising by dry weight approximately 0.5% to approximately 99% C20:5 n3 Eicosapentaenoic acid (EPA) and approximately 0.5% to approximately 99% C16:1 n7 palmitoleic acid (POA). Further exemplary algal fatty acid compositions may comprise one or more of the following by dry weight: less than approximately 5% arachidonic acid; substantially no docosahexaenoic acid; and/or less than approximately 10% saturated fatty acids. Further exemplary saturated fatty acyl moiety-rich algal compositions may be in a form of an ethyl ester (EE), a mono, di- or triacylglycerol (MAG, DAG, TAG), a phospholipid (PL), a galactolipid (GL), free fatty acid (FFA), or a sulfoquinovosyl diacylglycerol (SQDG).

The exemplary compositions herein may include algal fatty acid compositions comprising by dry weight approximately 0.5% to approximately 99% C18:1n9 Oleic acid (OA) and none, one or both of the following: 0.5% to approximately 99% C20:5 n3 Eicosapentaenoic acid (EPA), and approximately 0.5% to approximately 99% C16:1 n7 palmitoleic acid (POA). Further exemplary algal fatty acid compositions may comprise (in addition to the above) one or more of the following by dry weight: between approximately 0% and 99% arachidonic acid; between approximately 0% and 99% docosahexaenoic acid; and/or less than approximately 20% saturated fatty acids (including 0% saturated fatty acids or substantially saturated fatty acid free). According to further exemplary total algal oil compositions, the saturated fats may comprise PA. Further exemplary saturated fatty acyl moiety-rich algal compositions may be in a form of an ethyl ester (EE), a mono, di- or triacylglycerol (MAG, DAG, TAG), a phospholipid (PL), a galactolipid (GL), free fatty acid (FFA), or a sulfoquinovosyl diacylglycerol (SQDG).

The exemplary compositions herein may comprise a fatty acid composition comprising by dry weight approximately 0.5% to approximately 99% C20:5 n3 Eicosapentaenoic acid (EPA).

The exemplary compositions herein may comprise a whole algal biomass composition comprising at least approximately 10% lipids, at least approximately 15% carbohydrates, at least approximately 25% protein, at least approximately 3% moisture and at least approximately 5% ash.

The exemplary compositions herein may be used as feed, food, food supplements, beverages, beverage supplements, nutritional products, beauty products, cosmetic products, products for weight management, satiety products, products for athletic performance, pharmaceutical products, and/or medical products for mammalian use, including humans.

The exemplary compositions herein may be orally, topically, intravenously, and/or subcutaneously administered.

The exemplary compositions herein may be used for inhibiting inflammation of tissues of mammalian subjects by topical or oral administration. According to some exemplary methods, various exemplary compositions may be administered at approximately between 1 milligram per day and 100 grams per day, for periods ranging from one day to up to one year or more. Additionally, exemplary treatment methods may include periodically measuring a clinical marker of inflammation. In yet further exemplary treatment methods, the mammalian subject may have an inflammatory disease, including cardiovascular disease, diabetes, obesity, stroke, a metabolic syndrome, dementia, Alzheimer's disease, or cancer.

Some or all of the exemplary compositions herein may be in the form of capsules:

1. Having a wide range of capsule volumes;
2. Having a wide range in contents, ranging from 1 milligram to 500 grams of the various exemplary compositions herein; and/or
3. Having a wide range of percentage of capsule volume filled by the various exemplary compositions herein. For example, at least approximately 10% to approximately 90% or higher of volume of a particular capsule may be filled by one or more of the various exemplary compositions herein.

Some exemplary capsules comprising whole biomass may have at least approximately 500 mg of contents, and some exemplary capsules comprising EPA may have at least approximately 50 mg of contents.

Some or all of the exemplary compositions herein may comprise no or substantially no (for example, approximately less than 0.5%) DHA and low (for example, approximately 0% to 5%) ARA.

Some or all of the exemplary compositions herein may comprise a range (for example, approximately 0% to 99%) of saturated fats.

Some or all of the exemplary total algal oil compositions herein may have less than approximately 10% ARA.

Some or all of the exemplary whole biomass compositions herein may have at least approximately 3% moisture and at least approximately 5% ash.

FIG. 1 is a flow chart of an exemplary method for inhibiting inflammation of tissue of a mammalian subject.

At step 10, an effective dose is administered of a composition selected from any of:

a composition comprising by dry weight approximately 20% to approximately 97% algal C20:5 n3 Eicosapentaenoic acid (EPA);

a composition comprising by dry weight approximately 17% to approximately 90% algal C16:1 n7 palmitoleic acid (POA) and less than approximately 10% algal saturated fatty acids;

a composition comprising by dry weight approximately 17% to approximately 90% algal C16:1 n7 palmitoleic acid (POA) and substantially no algal saturated fatty acids;

a composition comprising a blend by dry weight of approximately 20% to approximately 97% algal C20:5 n3 Eicosapentaenoic acid (EPA) and approximately 17% to approximately 90% algal C16:1 n7 palmitoleic acid (POA); or a total algal oil composition comprising by total weight at least 20% algal EPA, at least 17% algal POA, less than approximately 10% ARA, and substantially no algal DHA and substantially no algal saturated fatty acids.

According to some exemplary methods, the effective dose is approximately between 20 milligrams per day and 5 grams per day. According to various exemplary methods, the effective dose of POA may range from approximately 1 gram per day to 3 grams per day, and may be as high as approximately 5 grams per day or higher. According to other exemplary methods, the effective dose of EPA may be as high as approximately 3 grams per day. In yet further exemplary methods, the effective dose may be based on other factors, such as subject age, gender, and/or weight.

At step 20, the selected composition is administered for a treatment period of at least 30 days.

At step 30, a clinical marker of inflammation may be measured on a first day of administration.

According to some exemplary methods, the clinical marker is any of weight, triglyceride level, total cholesterol, low-density lipoprotein, high-density lipoprotein, C-reactive protein, adiponectin, fatty acids, tumor necrosis factor alpha, C-peptide, interleukin 6, monocyte chemoattractant protein-1, insulin level, ghrelin, leptin or glucagon.

At step 40, the clinical marker of inflammation may be measured on day 30.

According to most exemplary methods, the clinical marker measurement indicates an improvement relative to a clinical marker measurement made before day 30. In yet further exemplary methods, the mammalian subject may be a human and may have an inflammatory disease, including cardiovascular disease, diabetes, obesity, strokes, a metabolic syndrome, dementia, Alzheimer's disease, and/or cancer.

Example One

Inflammation

Subject Population: Men and Women, with or without coronary artery disease.

Eligibility: diet stable, high triglyceride level (fasting triglyceride level ≥200 mg/dl and ≤2,000 mg/dl) and/or high total cholesterol (≥6.5 mmol/L).

Endpoint measurements: weight, triglyceride level ("TG"), low-density lipoprotein ("LDL"), high-density lipoprotein ("HDL"), total cholesterol ("TC"), C-reactive protein ("CRP"), adiponectin, and fatty acids.

Study design: double-blind, randomized placebo controlled trial.

Lipid-lowering agents included, and no medication added/changed during study.

Control arm: diet (based on American Heart Association ("AHA") guidelines) only.

Active arm: diet+POA (POA may be 500 milligrams/day, 1 gram/day, or 3 grams/day).

POA=highly purified (>80%) POA.

Wash out, 1 m→lead-in period (qualify lipid profiles)→qualified subjects enter double-blind RCT, 3 m→Washout, 3 m.

Anticipated results: improve markers of Inflammation.

For example, increase adiponectin, and increase serum POA, decrease CRP, TG, TC, LDL-C, serum PA, ↔HDL-C.

Example Two

Bread

For consuming 250 mg of POA per day, with bread providing 10-20% of the recommended 250 mg of POA requirement, utilize a 60% POA product in TG form, with two serving sizes as shown below:

| Bread | 25 mg serving of POA grams | 50 mg serving of POA grams |
|---|---|---|
| Wheat | 360 | 360 |
| Yeast | 1 | 1 |
| Water | 236 | 236 |
| Salt | 6 | 6 |
| sugar (brown, honey) | 12.6 | 12.6 |
| Butter | 15 | 15 |
| Milk | 120 | 120 |
| Palmitoleic acid | 0.0417 | 0.0833 |

Example Three

Beverage 12 fluid ounce bottle with 375 g smoothie.

|  | Grams | % |
|---|---|---|
| Whole Biomass | 18.75 | 5% |
| apple juice | 161.0625 | 42.95% |
| banana puree | 75 | 20% |
| mango puree | 37.5 | 10% |
| strawberry puree | 37.5 | 10% |
| beet juice | 18.75 | 5% |

-continued

|  | Grams | % |
|---|---|---|
| kale juice | 26.25 | 7% |
| vitamin C | 100 mg | 0.03% |
| Sunflower Lecithin | 100 mg | 0.03% |
| Totals | 374.8125 | 1 |

Example Four

Feed

|  | Grams | % |
|---|---|---|
| Whole Biomass | 0.965 | 3.5% |
| Corn grain | 0.45 | 55.0% |
| soybean meal | 0.585 | 41.5% |
| Total |  | 100.00% |

Example Five

Capsule 1000 milligram capsule with approximately 993 milligrams of ingredients:

| 880 mg/g Palmitoleic acid - EE | (88%) |
|---|---|
| 50 mg/g Saturated fats | (5%) |
| 25 mg/g Palmitic acid |  |
| 3 mg/g Omega- 6 |  |
| 2 mg ARA |  |
| 40 mg/g Omega -3 | (4%) |
| 12 mg/g EPA |  |
| 4 mg/g ALA |  |
| 0 mg/g DHA |  |

May include less than approximately 20 mg (2%) of alpha tocopherol (vitamin E) or another antioxidant.

Example Six

Dietary Endocrine Study

Three exemplary compositions, including:
1. An algal composition comprising by dry weight at least approximately 50% C16:1 n7 palmitoleic acid and less than approximately 10% saturated fatty acids;
2. An algal fatty acid composition comprising by dry weight approximately 0.5% to approximately 99% C20:5 n3 Eicosapentaenoic acid (EPA) and approximately 0.5% to approximately 99% C16:1 n7 palmitoleic acid (POA), and more specifically; and/or
3. An algal fatty acid composition comprising by dry weight approximately 0.5% to approximately 99% C20:5 n3 Eicosapentaenoic acid (EPA).

The exemplary compositions could be administered to rats at varying dosages ranging from approximately 50 mg/kg of body weight to 5000 mg/kg of body weight for twelve weeks. On a weekly basis, the following parameters could be determined (including before dosing):
1. Bodyweight, BMI, and anthropometric measurements;
2. Food and water consumption;
3. Blood glucose level;
4. Diabetes biomarkers, including insulin, ghrelin, leptin, and glucagon;
5. Inflammatory makers, including C-peptide, tumor necrosis factor alpha, and MCP-1; and
6. Fatty acid profile.

A comparison between inflammatory and diabetic biomarkers could be made between treated and untreated rats. It is expected that the treated rats will show a marked decrease in inflammatory and diabetic symptoms as evidenced by corresponding changes in the above-specified parameters.

Example Seven

Dietary Exercise Study

Three exemplary compositions, including:
1. An algal composition comprising by dry weight at least approximately 50% C16:1 n7 palmitoleic acid and less than approximately 10% saturated fatty acids;
2. An algal fatty acid composition comprising by dry weight approximately 0.5% to approximately 99% C20:5 n3 Eicosapentaenoic acid (EPA) and approximately 0.5% to approximately 99% C16:1 n7 palmitoleic acid (POA); and/or
3. An algal fatty acid composition comprising by dry weight approximately 0.5% to approximately 99% C20:5 n3 Eicosapentaenoic acid (EPA).

The exemplary compositions could be administered to various groups of rats comprising either lean or obese rats, at varying dosages ranging from approximately 50 mg/kg of body weight to 5000 mg/kg of body weight for twelve weeks. Exercise regimens could be varied between groups of rats. On a weekly basis, the following parameters could be determined (including before dosing):
1. Bodyweight, BMI and anthropometric measurements;
2. Food and water consumption;
3. Blood glucose level;
4. Diabetes biomarkers, including insulin, ghrelin, leptin, and glucagon;
5. Inflammatory makers, including C-peptide, tumor necrosis factor alpha, CRP, MCP-1, and adiponection;
6. Fatty acid/lipid profile, including FFA, LDL, HDL, cholesterol;
7. Omega 3 index; and
8. Lactate.

A comparison between inflammatory and exercise performance biomarkers could be made between treated, untreated, and sedentary rats. It is expected that the treated rats will show a marked decrease in inflammatory and diabetic symptoms as evidenced by corresponding changes in the above-specified parameters.

While various embodiments have been described above, it should be understood that they have been presented by way of example only, and not limitation. Thus, the breadth and scope of a preferred embodiment should not be limited by any of the above-described exemplary embodiments.

What is claimed is:
1. A method for reducing inflammation due to cardiovascular disease in a human subject having a cardiovascular disease, the method comprising administering a pharmaceutically effective dose to the human subject a composition of: a total algal oil composite comprising by total weight at least 20% algal EPA, 50% to 70% algal POA, 0% to 3% algal saturated fats, greater than 6.5% algal ARA, and substantially no algal DHA.

2. The method of claim 1, wherein the effective dose is approximately between 20 milligrams per day and 5 grams per day.

3. The method of claim 2, further comprising administering the composition for a treatment period of at least 30 days.

4. The method of claim 3, further comprising measuring a clinical marker of inflammation on a first day of administration.

5. The method of claim 4, wherein the clinical marker is total cholesterol.

6. The method of claim 3, further comprising measuring a clinical marker of inflammation on day 30.

7. The method of claim 6, wherein the clinical marker measurement indicates an improvement relative to a clinical marker measurement made before day 30.

8. The method of claim 1, wherein the composition is administered orally.

9. The method of claim 1, wherein the composition is any of a nutritional composition, medical composition, or pharmaceutical composition.

10. The method of claim 1, wherein each ingredient of the composition is in a form of an ethyl ester (EE).

11. A method for reducing in an obese human subject chronic inflammation due to obesity, the method comprising orally administering to the obese human subject on a daily basis for a treatment period of at least 30 days at least one capsule having at least approximately 25 percent of capsule volume comprising a pharmaceutically effective composition further comprising by dry weight approximately 90% palmitoleic acid, less than approximately 0.5% saturated fatty acids, less than approximately 2% arachidonic acid, substantially no docosahexaenoic acid, and less than approximately 10% eicosapentaenoic acid, wherein each ingredient of the composition is in a form of an ethyl ester (EE).

12. The method of claim 11, further comprising reducing an elevated marker of chronic inflammation.

13. The method of claim 12, wherein the elevated marker of chronic inflammation is IL6.

14. A method for reducing in a human subject having coronary artery disease inflammation due to coronary artery disease, the method comprising orally administering to the human subject on a daily basis for a treatment period of at least 30 days at least one capsule having at least approximately 25 percent of capsule volume comprising a pharmaceutically effective composition further comprising by dry weight approximately 90% palmitoleic acid, less than approximately 0.5% saturated fatty acids, less than approximately 2% arachidonic acid, substantially no docosahexaenoic acid, and less than approximately 10% eicosapentaenoic acid, wherein each ingredient of the composition is in a form of an ethyl ester (EE).

* * * * *